United States Patent [19]
Ottea et al.

[11] Patent Number: 6,150,404
[45] Date of Patent: Nov. 21, 2000

[54] METHOD TO DIAGNOSE METABOLIC PYRETHROID INSECTICIDE RESISTANCE

[75] Inventors: James A. Ottea; Guomin Shan, both of Baton Rouge, La.

[73] Assignee: Board of Supervisors of Louisiana State University and Agricultural and Mechanical College, Baton Rouge, La.

[21] Appl. No.: 09/212,441

[22] Filed: Dec. 16, 1998

Related U.S. Application Data

[60] Provisional application No. 60/109,811, Dec. 22, 1997.

[51] Int. Cl.$^7$ ............................ A01N 43/30; A01N 53/00
[52] U.S. Cl. ........................................... 514/465; 514/531
[58] Field of Search ................................... 514/521, 465, 514/531

[56] References Cited

U.S. PATENT DOCUMENTS 4,183,950  1/1980  Nauman et al. ......................... 424/305

OTHER PUBLICATIONS

Shan et al, Biological Activity of Pyrethroid Analogs, J. Agric. Food Chem., vol. 45, pp. 4466–4473, 1997.

Ackermann, P. et al., "The Optical Isomers of α–Cyano–3–Phenoxybenzyl 3–(1,2–dibromo–2, 2–dichloroethyl)– 2,2–dimethylcyclopropanecarboxylate and Their Insecticidal Activities," Pestic. Sci., vol. 11, pp. 169–179 (1980).

Behrenz, W. et al., "Properties and Potentialities of NAK 1654 (Fenfluthrin), a New Pyrethroid for the Control of Household, Public Health, and Stored–Product Pests," Pflanzenschutz–Nachrichten, vol. 35, pp. 309–349 (1982).

Brown, T. et al., "Synergism by Propynly Aryl Ethers in Permethrin–Resistant Tobacco Budworm Larvae Heliothis virescens," Pestic. Sci., vol. 43, pp. 323–331 (1996).

Casida, J. et al., "Metabolic Chemistry of Pyrethroid Insecticides," Pestic. Sci., vol. 11, pp. 257–269 (1980).

Forrester, N. et al., "Pyrethroid Resistance: Resistance Breaking Pyrethroids," Bull. Entomol. Res. Supp. Ser., vol. 1, pp. 83–96 (1993).

Graves, J. et al., "Status of Pyrethroid Resistance in Tobacco Budworm and Bollworm in Louisiana," Proc. Beltwide Cotton Prod. Res. Conf., National Cotton Council, Memphis, TN, pp. 638–641 (1991).

Gunning, R. et al., "Esterases and Esfenvalerate Resistance in Australian Helicoverpa armigera (Hubner) Lepidoptera: Noctuidae," Pestic. Biochem. Physiol., vol. 54, pp. 12–23 (1996).

Leahey, J., "Metabolism and Environmental Degradation," J. Leahey (ed.) The Pyrethroid Insecticides, pp. 263–342 (1985).

Lee, K. et al., "Metabolism of trans Cypermethrin by Helicoverpa armigera and Heliothis virescens," Pestic. Biochem. Physiol., vol. 34, pp. 49–57 (1989).

Little, E. et al., Evidence for an Enhanced Metabolism of Cypermethrin by a Monooxygenase in a Pyrethroid–Resistant Strain of the Tobacco Budworm (Heliothis virescens), Pestic. Biochem. Physiol., vol. 34, pp. 58–68 (1989).

Ottea, J., CRIS report (Feb. 12, 1997).

Ottea, J. et al., "Biochemical and Physiological Mechanisms of Pyrethroid Resistance in Heliothis virescens (F.)," Pest. Biochem. Phys., vol. 51, pp. 117–128 (1995).

Scott, J. et al., "Mechanisms Responsible for High Levels of Permethrin Resistance in the House Fly," Pestic. Sci., vol. 17, pp. 195–206 (1986).

Scott, J. et al., "Insecticidal Activity of Substituted Benzyl Dichlorovinylcyclopropane Carboxylates on Susceptible and kdr–Resistant Strains of the Southern House Mosquito, Culex quinquefasciatus," J. Pestic. Sci., vol. 11, pp. 475–477 (1986).

Shan, G. et al., "Development of Pyrethroid Analogs for Diagnosis of Resistance Mechanisms in the Tobacco Budworm, Heliothis virescens (F.)," Proc. Beltwide Cotton Conferences (1977).

Shan, G. et al., "Biological Activity of Pyrethroid Analogs in Pyrethroid–Susceptible and –Resistant Tobacco Budworms, Heliothis virescens (F.)," J. Agric Food Chem., vol. 45, pp. 4466–4473 (1997).

Shono, T. et al., "Metabolism of trans and cis Permethrin, trans and cis Cypermethrin and Decamethrin by Microsomal Enzymes," J. Agric. Food Chem. vol. 27, pp. 316–325 (1979).

Shono, T. et al., "Metabolism of Permethrin Isomers in American Cockroach Adults, House Fly Adults, and Cabbage Looper Larvae," Pestic. Biochem. Physiol., vol. 9, pp. 96–106 (1978).

Soderlund, D. et al., "Metabolism of Fenvalerate by Resistant Colorado Potato Beetles," J. Agric. Food Chem. vol. 35, pp. 100–105 (1987).

Primary Examiner—Jose' G. Dees
Assistant Examiner—Alton Pryor
Attorney, Agent, or Firm—John H. Runnels

[57] ABSTRACT

The phenoxybenzyl moiety of conventional pyrethroids is a major site of oxidative metabolism in resistant tobacco budworms, Heliothis virescens (F.). This group was replaced with several P450 monooxygenase-inhibiting or oxidatively blocked groups. Several isomers were tested as insecticides or synergists for insecticides against tobacco budworms that were insecticide-susceptible or that expressed metabolic resistance to cypermethrin. Several compounds with insecticidal and synergistic activities were found. Activity was dependent on both geometric and stereochemical configurations. These compounds may be used in diagnosing the mechanism of resistance in field strains with acquired resistance to pyrethroids. Knowledge of the mechanism underlying acquired insecticide resistance helps farmers to control emerging resistant strains.

11 Claims, 2 Drawing Sheets

| COMPOUNDS | X | R |
|---|---|---|
| Cypermethrin | CN |  |
| PFP-PA (Fenflluthrins 1,2, and 3) | H |  |
| MDP-PA (1-3) | H |  |
| CMDP-PA (4-6) | CN | |
| CPP-PA (7-12) | CN |  |

METHOD TO DIAGNOSE METABOLIC PYRETHROID INSECTICIDE RESISTANCE

The benefit of the Dec. 22, 1997 filing date of provisional application Ser. No. 60/109,811 is claimed under 35 U.S.C. §119(e).

This development of this invention was partially supported by the Government under HATCH finding awarded by the Department of Agriculture to contractor Louisiana State University Agricultural Center. The Government has certain rights in this invention.

This invention pertains to the diagnosis of mechanisms underlying acquired resistance to pyrethroid insecticides, to facilitate insecticide resistance management practices.

The tobacco budworm, *Heliothis virescens* (F.), was first recognized as a pest of cotton in 1934, and has become one of the most important insects attacking cotton in the United States. This pest, together with the cotton bollworm, *Helicoverpa zea* (Boddie), caused almost one-third of all insect damage to United States cotton during the 1990s. Development of insecticide resistance is a major contributor to this damage.

Development of insecticide resistance is generally due to one or more of three major mechanisms: reduced cuticular penetration, enhanced metabolic detoxication, and reduced target site sensitivity. Effective insecticide resistance management requires monitoring the susceptibility of tobacco budworms to insecticides, and identifying the mechanism underlying any developing resistance traits. By understanding the mechanism underlying resistance, insect pests may be better controlled. For example, one can manage metabolic resistance or reduced target site sensitivity by using a synergist, or by using an insecticide from a different chemical class, respectively.

Studies with *H. virescens* have found that resistance to pyrethroids, which are widely used against cotton pests in the United States, has been associated with each of these three resistance mechanisms. Pyrethroid toxicity has been enhanced in biological assays on field-collected tobacco budworms by using cytochrome P450 monooxygenase inhibitors such as piperonyl butoxide (PBO) and propynyl ethers as synergistic agents. Biochemical and pharmacokinetic studies have shown the importance of cytochrome P450 monooxygenases in pyrethroid resistance in laboratory and field-collected strains of *H. virescens*. The oxidative metabolism of pyrethroids by these enzymes apparently occurs predominantly at the 2' and 4' carbons of the phenoxybenzyl group found in many commercial pyrethroids.

Prior methods for characterizing resistance mechanisms in field populations of the tobacco budworm have included bioassays with combinations of insecticides and synergists, and biochemical assays of the activities of enzymes associated with insecticide metabolism. However, there can be multiple forms of these enzymes, with differing substrate specificities, and differing susceptibilities to inhibition by synergists. Thus the usefulness of these assays is limited by the reliability of the model substrates and synergists as indicators of toxicologically significant enzyme activities. The usefulness of results from bioassays with insecticide/synergist combinations is further limited by nonmetabolic effects of these compounds, and by the lack of structural similarity between conventional synergists (such as PBO and propynyl ethers) and pyrethroid insecticides.

Metabolic mechanisms are a major source of insect resistance to pyrethroids. Oxidative metabolism can occur at the 2', 4', and 6 positions of the phenoxybenzyl moiety, or in the two geminal methyl groups attached to the cyclopropane ring. See generally T. Shono et al., "Metabolism of Permethrin Isomers in American Cockroach Adults, House Fly Adults, and Cabbage Looper Larvae," *Pestic. Biochem. Physiol.*, vol. 9, pp. 96–106 (1978); T. Shono et al., "Metabolism of trans and cis Permethrin, trans and cis Cypermethrin and Decamethrin by Microsomal Enzymes," *J. Agric. Food Chem.* vol. 27, pp. 316–325 (1979); J. Casida et al., "Metabolic Chemistry of Pyrethroid Insecticides," *Pestic. Sci.*, vol. 11, pp. 257–269 (1980); and J. Leahey, "Metabolism and Environmental Degradation," pp. 263–342 in J. Leahey (ed.), *The Pyrethroid Insecticides* (1985). Oxidative diphenyl ether cleavage has been reported from a study with fenvalerate in the Colorado potato beetle, *Leptinotarsa decemlineata*. D. Soderlund et al., "Metabolism of Fenvalerate by Resistant Colorado Potato Beetles," *J. Agric. Food Chem.* vol. 35, pp. 100–105 (1987).

K. Lee et al., "Metabolism of trans Cypermethrin by *Helicoverpa arinigera* and *H. virescens*," *Pestic. Biochem. Physiol.*, vol. 34, pp. 49–57 (1989); and E. Little et al., "Evidence for an Enhanced Metabolism of Cypermethrin by a Monooxygenase in a Pyrethroid-Resistant Strain of the Tobacco Budworm (*Heliothis virescens* F.)," *Pestic. Biochem. Physiol.*, vol. 34, pp. 58–68 (1989) suggested that the 2' and 4' positions on the phenoxybenzyl moiety of cypermethrin are the main sites of oxidative metabolism in *H. virescens*, while oxidation at the geminal dimethyl groups is less important.

N. Forrester et al., "Pyrethroid Resistance: Resistance Breaking Pyrethroids," *Bull. Entomol. Res. Supp. Ser.*, vol. 1, pp. 83–96 (1993) disclosed several structural modifications to pyrethroid compounds, some of which were reported to overcome oxidative metabolic pyrethroid resistance in field populations of the moth *Helicoverpa armigera* in Australia.

J. Scott et al., "Mechanisms Responsible for High Levels of Permethrin Resistance in the House Fly," *Pestic. Sci.*, vol. 17, pp. 195–206 (1986) reported that permethrin resistance in a pyrethroid-selected strain of the house fly was attributable to mechanisms for metabolic detoxification via the mixed-function oxidase system, target site insensitivity, and decreased cuticular penetration. The resistant strain was reported to have varying resistance ratios (as compared to a susceptible strain) to 18 pyrethroids with differing structures.

W. Behrenz et al., "Properties and Potentialities of NAK 1654 (Fenfluthrin), a New Pyrethroid for the Control of Household, Public Health, and Stored-Product Pests," *Pflanzenschutz-Nachrichten*, vol. 35, pp. 309–349 (1982) discloses the use of NAK (1R, trans-fenfluthrin) as an insecticide. See also U.S. Pat. No. 4,183,950.

T. Brown et al., "Synergism by Propynyl Aryl Ethers in Permethrin-Resistant Tobacco Budworm Larvae, *Heliothis virescens*," *Pestic. Sci.*, vol. 43, 323–331 (1996) reported the activity of TCPB and other synergists against pyrethroid-resistant *H. virescens*. (Note: A listing of abbreviations, such as "TCPB," appears at the end of this specification.) J. Graves et al., "Status of Pyrethroid Resistance in Tobacco Budworm and Bollworm in Louisiana," pp. 638–641 in *Proc. Beltwide Cotton Prod. Res. Conf.*, National Cotton Council, Memphis, Tenn. (1991); and R. Gunning et al., "Esterases and Esfenvalerate Resistance in Australian *Helicoverpa armigera* (Hübner) Lepidoptera: Noctuidae," *Pestic. Biochem. Physiol.*, vol.54, pp.12–23 (1996) reported that esterases were involved in pyrethroid resistance in adult *H. virescens* and in larval *H. armigera*, respectively.

P. Ackermann et al., "The Optical Isomers of α-Cyano-3-Phenoxybenzyl 3-(1,2-dibromo-2,2-dichloroethyl)-2,2- dimethylcyclopropanecarboxylate and Their Insecticidal Activities," *Pestic. Sci.* vol. 11, pp. 169–179 (1980) reported the effects of stereochemical conformation on the toxicity of a brominated analog of cypermethrin in pyrethroid-susceptible *H. virescens*.

PBO has been reported to suppress resistance to cypermethrin in *H. armigera*, to permethrin in house flies, and to permethrin in the southern house mosquito *Culex quinquasciatus*, but to be relatively ineffective as a synergist of fenfluthrin toxicity. See N. Forrester et al., "Pyrethroid Resistance: Resistance Breaking Pyrethroids," *Bull. Entomol. Res. Supp. Ser.* vol. 1, pp. 83–96 (1993); and J. Scott et al., "Insecticidal Activity of Substituted Benzyl Dichlorovinylcyclopropanecarboxylates on Susceptible and kdr-Resistant Strains of the Southern House Mosquito, *Culex quinquefasciatus*," *J. Pestic. Sci.*, vol. 11, 475–477 (1986).

J. Ottea et al., "Biochemical and Physiological Mechanisms of Pyrethroid Resistance in *Heliothis virescens* (F.)," *Pest. Biochem. Phys.*, vol. 51, pp. 117–128 (1995) discloses work concluding that multiple mechanisms can be responsible for pyrethroid resistance in *H. virescens*, including higher metabolic rates, higher levels of excretion, and reduced neuronal sensitivity. Metabolic rates of cypermethrin were measured by extraction and analysis of metabolites from carcass homogenates and excreta.

G. Shan et al., "Biological Activity of Pyrethroid Analogs in Pyrethroid-Susceptible and Resistant Tobacco Budworms, *Heliothis virescens* (F.)," *J. Agric Food Chem.*, vol. 45, pp. 4466–4473 (1997); G. Shan et al., "Development of Pyrethroid Analogs for Diagnosis of Resistance Mechanisms in the Tobacco Budworm, *Heliothis virescens* (F.)," *Proc. Beltwide Cotton Conferences* (1997); and J. Ottea, CRIS report (Feb. 12, 1997) report certain work from our research group related to that reported in the present specification.

There is a continuing need for new methods to diagnose mechanisms underlying acquired insecticide resistance in the tobacco budworm and the cotton bollworm.

We have discovered new methods for detecting and diagnosing metabolic resistance to pyrethroids using various esters of 3-(2,2-dichlorovinyl)-2,2-dimethylcyclopropane carboxylic acid (permethric acid; PA). These esters contain enzyme-inhibiting side chains or groups that block potential sites of enzymatic metabolism. Accurate diagnosis of the mechanisms underlying acquired insecticide resistance permits better insecticide resistance management practices.

MATERIALS AND METHODS

Figure 1:
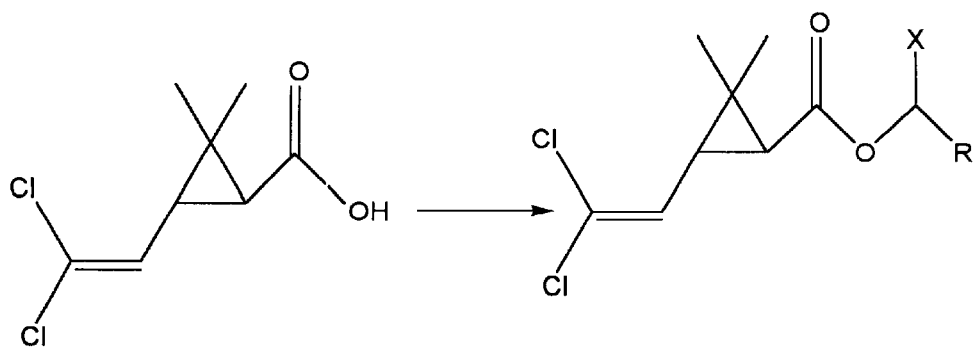
FIG. 1 depicts several of the compounds used in this study.
Figure 1:
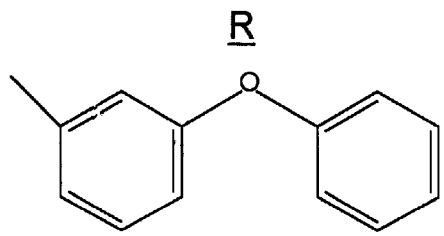
Figure 1:
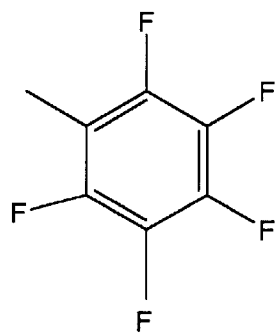
Figure 1:
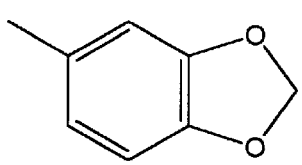
Figure 1:
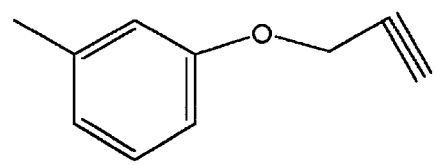

Chemicals. Cypermethrin (technical grade; a racemic mixture of trans/cis, 1R/S and α-R/S isomers) was obtained from FMC Corporation (Princeton, N.J.). The methyl ester of PA (methyl 3-(2,2-dichlorovinyl)-2,2-dimethylcyclopropane carboxylate; cis/trans=40160) was purchased from Fisher Scientific (Pittsburgh, Pa.). Pentafluorobenzyl alcohol, piperonyl alcohol, piperonal, 2,3,6-trichlorophenol, sesamol, 3-hydroxybenzaldehyde, propargyl bromide, (+)-ephedrine, and (−)-ephedrine were purchased from Aldrich Chemical Company (Milwaukee, Wisc.). Piperonyl butoxide (PBO) was purchased from ChemService (West Chester, Pa.). S,S,S-tributyl phosphorotrithioate (DEF) was kindly provided by Bayer Corporation (Kansas City, Mo.). All other chemicals were of analytical quality, and were purchased from commercial suppliers.

Instruments. $^1$H NMR spectra were measured on a Brucker AC-200 spectrometer using tetramethylsilane as an internal standard. Optical rotations were measured on a Jasco Digital Polarimeter (Model DIP-370, Na 589 nm). Compounds were analyzed by gas chromatography using a capillary column (DB-5, 20 m×0.18 mm) with the following temperature programming: $T_{init}$, 40° C. for 3 min; then 20° C./min to $T_{final}$, 280° C. Detection of compounds following the gas chromatograph was performed with a Hewlett-Packard 5971A mass selective detector.

Insects. Pyrethroid-susceptible and pyrethroid-resistant laboratory strains of *H. virescens* were used. The susceptible "LSU" strain was established in 1977 and has been reared in the laboratory since that time without exposure to insecticides. The susceptible LSU strain was reported in B. Leonard et al., "Evaluation of Field Populations of Tobacco Budworm and Bollworms for Resistance to Selected Insecticides," *J. Econ. Entomol.* vol. 81, 1521–1528 (1988).

The resistant "Pyr-R" strain was derived from a field collection made in August 1995 at the Louisiana State University Agricultural Center Red River Research Station (Bossier City, La.). Insects from this collection were reared for one generation. Fifth stadium larvae were then selected for resistance by exposure to cypermethrin (1.75 μg/larva) for three generations. Resistance to pyrethroid insecticides has been reported to result from reduced neuronal sensitivity in house flies. This trait is recessive in the house fly. In an effort to "dilute" any contribution to resistance in the Pyr-R strain that may have resulted from such reduced neuronal sensitivity, survivors of this selection were crossed with LSU insects, and their $F_1$ progeny were selected as third stadium larvae with 1.0 μg cypermethrin/larva, a dose that is 21 times the $LD_{50}$ for the susceptible LSU larvae. Preliminary results from neurophysiological and molecular genetic assays suggest that reduced neuronal sensitivity was not a significant resistance mechanism in Pyr-R insects.

Preparation of PA. The methyl ester of PA (22.3 g, 0.1 mole), sodium hydroxide (12 g, 0.3 mole), and ethanol-water (1:1; 250 mL) were mixed together and then refluxed overnight. The mixture was concentrated under reduced pressure, diluted with water, and extracted with ethyl ether ($Et_2O$, 2×40 mL). The aqueous layer was acidified with concentrated HCl, and the precipitate was extracted into $Et_2O$ (2×50 mL), washed with water, and dried overnight ($Na_2SO_4$). The $Et_2O$ was removed to leave a solid product, which was recrystallized from hexane-ether (1:1). Yield: 18.5 g, 83%, m.p. 55–58° C.

Separation of trans- and cis-PA. The geometric isomers of PA were separated by the method of E. Foggassy et al., "Process for the Separation of Isomeric Cyclopropane-Carboxylic Acids," U.S. Pat. No. 4,599,444 (1986). PA (20.9 g, 0.1 mole) was mixed with benzene (100 mL) and stirred at 27° C. for 5 h. The suspension was filtered, and then recrystallized from benzene to give 3.9 g (47%) of pure cis-PA, m.p. 94–96° C.

To isolate the trans isomer, PA (20.9 g, 0.1 mole) was stirred with petroleum ether (100 mL) at 30° C. for 5 h. The resulting suspension was filtered to yield 4.2 g solid product, which was recrystallized from hexane to give 3.6 g (29%) pure trans-PA, m.p. 84–87° C.

Separation of 1R, cis- and 1S, cis-PA. The two cis enantiomers of PA were resolved prior to esterification by the method of J. Jolly et al., "Resolution of D, L-cis and D, L-trans 2,2-Dimethyl-3-(2,2-Dihalovinyl)-Cyclopropane-1-Carboxylic Acids and Salts Thereof," U.S. Pat. No. 4,328, 173 (1982). Cis-PA (10 g, 0.05 mole) was dissolved in dichloroethane (100 mL), and then either (−)- or (+)-ephedrine (8.25 g, 0.05 mole) was added. The mixture was stirred at 20° C. for 1 h and then filtered under reduced pressure. The solid crude product was recrystallized from dichloroethane to give 6.5 g (30%) of pure (−)-ephedrine-(+)-cis-permethric salt or 6.6 g of (+)-ephedrine-(−)-cis-permethric salt. The salts were dissolved in methylene chloride (25 mL), and stirred with HCl (2 M, 30 mL) at 20° C. for 15 min, and the aqueous phase was extracted with methylene chloride. The combined organic phases were washed with water, dried over $Na_2SO_4$, and evaporated to dryness to obtain 2.9 g (29% yield) of 1R, cis-PA with an optical purity of 99.4%, and a specific rotation of $[\alpha]_D^{20}$=+32.1° (c=1.0, $CHCl_3$; lit. $[\alpha]_D$=+32.20). For the 1S, cis-PA, the yield was 2.7 g (27%), with an optical purity of 91.6% and a specific rotation of $[\alpha]D^{20}$=−29.5° (c=1.0, $CHCl_3$; lit. $[\alpha]_D$=−32.2°).

A similar approach was used to separate 1R, trans- and 1S, trans-PA. Whereas the 1R trans enantiomer was not separated, a small quantity of 1S, trans-PA was obtained (<10% yield) with an optical purity of 97.0% and a specific rotation of $[\alpha]D^{20}$=−34.6° (c=1.0, $CHCl_3$; lit. $[\alpha]_D$=−35.6°). This material was esterified and used as a standard for identification of trans isomers (see below).

Synthesis of 3-Propargyloxybenzaldehyde. Potassium tert-butoxide (6.16 g, 0.055 mole), 3-hydroxybenzaldehyde (6.1 g, 0.05 mole), and dry dimethylformamide (DMF, over $Na_2SO_4$; 30 mL) were stirred briefly at 25° C., and then propargyl bromide (6.6 g, 0.055 mole) was added in 30 mL of dry DMF according to the method of F. Albericio et al., "Preparation and Application of the 5-(4-(9-Fluorenylmethyloxycarbonyl)-Aminomethyl-3,5-Dimethoxyphenoxy)-ValericAcidHandle for the Solid Phase Synthesis of C-Terminal Peptide Amides under Mild Conditions," *J. Org. Chem.* vol. 55, pp. 3730–3743 (1990). The reaction mixture was heated to 110° C. for 8 h, and the solvent was then removed under high vacuum. Ethyl acetate was added, inorganic salts were removed by filtration, and the organic extract was washed sequentially with water, 2 M NaOH, and saturated aqueous NaCl. The organic phase was dried overnight ($MgSO_4$), and the solvent was removed to yield a yellow liquid that was purified by silica gel chromatography using hexane-ethyl acetate (8.5:1.5) as the eluting solvent. Yield: 6.5 g (81%). $^1H$ NMR ($CDCl_3$): d 2.54 (t, 1H, CH), 4.73 (t, 2H,—$OCH_2$—), 7.2–7.48 (m, 4H, Aromatics), 9.96 (s, 1H, CHO). GC-MS (m/z): $M_+$=160.

General Esterification Procedures. Two general routes of synthesis were used to esterify PA and various alcohols (see generally FIG. 1).

Method 1. Mixed isomers of 3,4-methylenedioxyphenyl methyl 3-(2,2-dichlorovinyl)-2,2-dimethylcyclopropanecarboxylate (MDP-PA); and pentafluorophenyl methyl 3-(2,2-dichlorovinyl)-2,2-dimethyl cyclopropane carboxylate (PFP-PA) were made by the method of D. Karanewsky et al., "Synthesis of Phosphonic Monoesters from Phosphonous Acids," *Tetrahedron Lett.,* vol. 27, pp. 1751–1754 (1986). PA (0.01 mole) and alcohols (0.011 mole) were dissolved in dry chloroform (20 mL) at room temperature, and then dicyclohexylcarbodiimide (DCC; 0.011 mole) and N,N-dimethylaminopyridine (DMAP; 0.001 mol) were added. After stirring at room temperature for 3 h, the mixture was diluted with chloroform (20 mL), filtered, and washed sequentially with 5% HCl, water, 10% aqueous sodium bicarbonate, and water. The organic phase was dried over $Na_2SO_4$, and the solvent was removed to yield a crude product that was purified by silica gel chromatography using ethyl acetate-hexane (30:70, v/v) as the eluting solvent. Yields: trans MDP-PA (74%), cis MDP-PA (70%), trans PFP-PA (75%), cis PFP-PA (68%).

Method 2. Isomers of PA were esterified with piperonal or 3-propargyloxybenzaldehyde using the method of B. Hu et al., "The Synthesis of Pyrethroids of 2-(3,4-Methylene Dioxyphenyl)-3-Methylbutyric Acid," Acta Agriculturae Universitatis Pekinensis, vol. 11, pp. 167–170 (1985) to yield α-cyano-3,4-methylenedioxybenzyl 3-(2,2-dichlorovinyl)-2,2-dimethylcyclopropanecarboxylate (CMDP-PA) and α-cyano-3-propargyloxybenzyl 3-(2,2-dichlorovinyl)-2,2-dimethyl cyclopropanecarboxylate (CPP-PA). PA (0.05 mole) was dissolved in $CHCl_3$ with 1 drop of DMF at 18° C., and thionyl chloride ($SOCl_2$; 0.3 mole) was added drop-wise over 5 min. The mixture was stirred at 40° C. for 2–3 h, cooled to room temperature. The solvent and excess $SOCl_2$ were then removed under high vacuum to give a hazy oil of the acid chloride (yield>95%). To this acid chloride, the appropriate benzaldehyde (0.05 mole), 18-crown-6 (2 mmol), and toluene (60 mL) were added. This mixture was heated to 25–30° C., and NaCN (0.065 mole, in 10 mL of water) was then added drop-wise over 5 min. The mixture was stirred at 3540° C. for 4–5 h, cooled, and diluted with water. The organic phase was washed sequentially with 10% HCl, water, 10% $Na_2CO_3$, water, and saturated aqueous NaCl. The organic phases were dried over $Na_2SO_4$ for two days, and solvent was removed over high vacuum to obtain a crude product, which was purified by silica gel chromatography using hexane-ethyl acetate (7:3) as the eluting solvent. Yields: trans CPP-PA (75%), cis CPP-PA (72%), trans CMDP-PA (81%), cis CMDP-PA (73%).

All trans isomers and α(RS), 1R, and cis enantiomers were separated after esterification by chiral HPLC using a Chiralcel OD HPLC column (Cellulose tris-(3,5-dimethylphenyl carbamate) on a 10 μm silica-gel substrate, 250 mm×20 mm; J. T. Baker, Phillipsburg, Pa.). The mobile phase ranged from 90:10 to 70:30 (hexane: isopropanol), and the amount of compound per injection was between 10 to 100 mg. See Table 1. The absolute configuration of the α carbon was assigned according to the method of M. Elliott et al., "The Pyrethrins and Related Compounds. Part XXII. Preparation of Isomeric Cyano-Substituted 3-Phenoxybenzyl Esters," *Pestic. Sci.,* vol. 9, pp. 105–111 (1978), based on retention times following separation by chiral HPLC and analysis of NMR spectra. The physical properties of isomers are shown in Table 2.

TABLE 1

Conditions for HPLC separation of enantiomers

| Compound | X | R[a] | Stereochemistry in Alcohol | Stereochemistry in Acid | Mobile phase hexane: isopropanol | Flow-rate (mL/min) | $t_R$ (min) |
|---|---|---|---|---|---|---|---|
| Fenfluthrin 1 | H | PFP | — | trans, 1S | 80:20 | 3.0 | 12 |
| Fenfluthrin 2 | H | PFP | — | trans, 1R | 80:20 | 3.0 | 14 |
| Fenfluthrin 3 | H | PFP | — | cis, 1R | — | — | — |
| 1 | H | MDP | — | trans, 1S | 80:20 | 5.0 | 11.5 |
| 2 | H | MDP | — | trans, 1R | 80:20 | 5.0 | 14.8 |
| 3 | H | MDP | — | cis, 1R | — | — | — |

TABLE 1-continued

Conditions for HPLC separation of enantiomers

| Compound | X | R[a] | Stereochemistry in Alcohol | Stereochemistry in Acid | Mobile phase hexane:isopropanol | Flow-rate (mL/min) | $t_R$ (min) |
|---|---|---|---|---|---|---|---|
| 4 | CN | MDP | αR/S | trans, 1R/S | — | — | — |
| 5 | CN | MDP | αS | cis, 1R | 90:10 | 4.25 | 17.2 |
| 6 | CN | MDP | αR | cis, 1R | 90:10 | 4.25 | 14.0 |
| 7 | CN | PP | αS | trans, 1R | 70:30 | 5.0 | 13.2 |
| 8 | CN | PP | αR | trans, 1R | 85:15 | 3.5 | 20.0[b] |
| 9 | CN | PP | αR | trans, 1S | 85:15 | 3.5 | 18.6[b] |
| 10 | CN | PP | αS | trans, 1S | 70:30 | 5.0 | 36.8 |
| 11 | CN | PP | αR | cis, 1R | 70:30 | 5.0 | 14.4 |
| 12 | CN | PP | αS | cis, 1R | 70:30 | 5.0 | 34.2 |

[a] PFP = pentafluorophenyl;
MDP = 3,4-methylenedioxyphenyl;
PP = 3-propargyloxyphenyl.
[b] A retention time of 7.2 min was measured for compounds 8 and 9 with 70:30 (hexane:isopropanol)

TABLE 2

Physical data for pyrethroid analogs

| | | | | | | | | | | | | |
|---|---|---|---|---|---|---|---|---|---|---|---|---|
| | | | | Alcohol | | | Acid | | | | | |
| | | | | | | | | | | | | |
| | | | | | | | | | | $^1$H-NMR peaks in CDCl$_3$ | | |
| Compound | [α]D[a] | GC $t_R$ (mins) | MS(m/z) (M$^{+\cdot}$) | Aromatics (m) | Hα (s) | others | H$_1$ (d) | H$_3$ (q) | vinyl (d) | 1(s) | C2—CH$_3$'s | 2(s) |
| Fenfluthrin 1 | 14.6 | 12.8 | 389 | — | 5.19 | — | 1.60 | 2.20 | 5.60 | 1.18 | | 1.27 |
| Fenfluthrin 2 | -13.9 | 12.8 | 389 | — | 5.19 | — | 1.60 | 2.20 | 5.60 | 1.18 | | 1.27 |
| Fenfluthrin 3 | -3.0 | 12.7 | 389 | — | 5.19 | — | 1.80 | 2.10 | 6.20 | | 1.24 | |
| 1 | 22.2 | 15.3 | 343 | 6.7–6.9 | 5.0 | 6.0(s, 2H, OCH$_2$0) | 1.62 | 2.25 | 5.60 | 1.19 | | 1.28 |
| 2 | -21.9 | 15.3 | 343 | 6.7–6.9 | 5.0 | 6.0(s, 2H, OCH$_2$0) | 1.62 | 2.25 | 5.60 | 1.19 | | 1.28 |
| 3 | -0.7 | 15.4 | 343 | 6.7–6.9 | 5.0 | 6.0(s, 2H, OCH$_2$0) | 1.84 | 2.05 | 6.3 | | 126 | |
| 4 | — | 16.3 | 368 | 6.8–7.0 | 6.3 | 6.0(s, 2H, OCH$_2$0) | 1.60 | 2.30 | 5.60 | | 1.8–1.27[b] | |
| 5 | 35.4 | 16.2 | 368 | 6.8–7.0 | 6.17 | 6.0(s, 2H, OCH$_2$0) | 1.85 | 2.10 | 6.29 | 1.19 | | 1.28 |
| 6 | -46.1 | 16.2 | 368 | 6.8–7.0 | 6.15 | 6.0(s, 2H, OCH$_2$0) | 1.85 | 2.10 | 6.25 | | 1.19 | |
| 7 | -13.0 | 16.2 | 378 | 7.1–7.4 | 6.40 | 2.5(d, 1H, CH), 4.7(s, 2H, CH$_2$) | 1.70 | 2.30 | 5.60 | 1.19 | | 1.26 |
| 8 | -21.6 | 16.2 | 378 | 7.1–7.4 | 6.40 | 2.5(d, 1H, CH), 4.7(s, 2H, CH$_2$) | 1.70 | 2.30 | 5.60 | 1.22 | | 1.33 |
| 9 | 12.0 | 16.2 | 378 | 7.1–7.4 | 6.40 | 2.5(d, 1H, CH), 4.7(s, 2H, CH$_2$) | 1.70 | 2.30 | 5.60 | 1.19 | | 1.26 |
| 10 | 25.8 | 16.2 | 378 | 7.1–7.4 | 6.40 | 2.5(d, 1H, CH), 4.7(s, 2H, CH$_2$) | 1.70 | 2.30 | 5.60 | 1.22 | | 1.33 |
| 11 | -19.5 | 16.0 | 378 | 7.0–7.4 | 6.30 | 2.5(d, 1H, CH), 4.7(s, 2H, CH$_2$) | 1.90 | 2.10 | 6.10 | | 1.30 | |
| 12 | 25.4 | 16.0 | 478 | 7.0–7.4 | 6.30 | 2.5(d, 1H, CH) 4.7(s, 2H, CH$_2$) | 1.90 | 2.10 | 6.10 | | 1.21 | |

[a] c = 1.0, CHCl$_3$, 20° C.
[b] containing 4 singlets: 1.18, 1.22, 1.26 and 1.33

Figure 2:
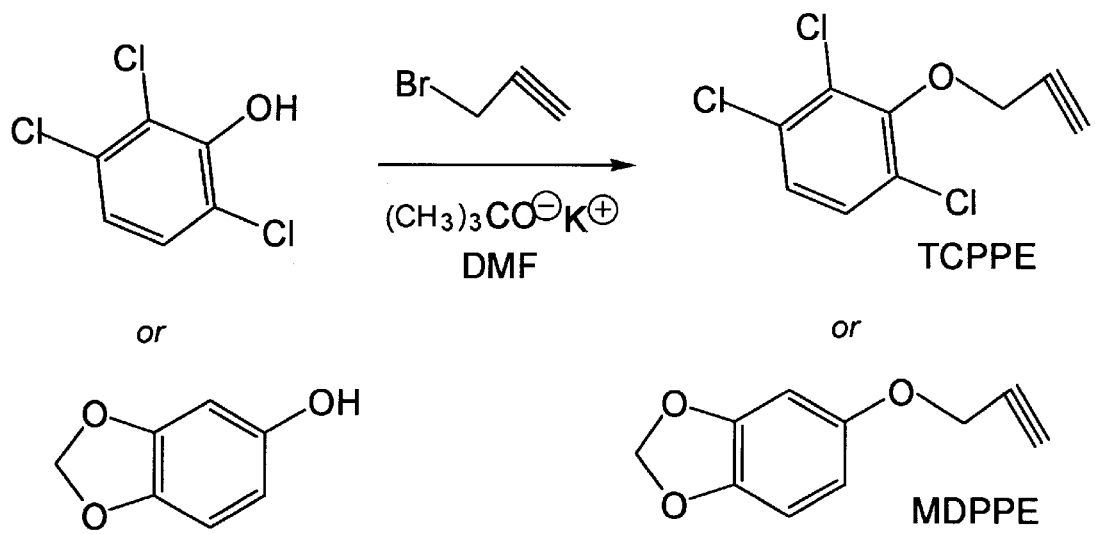
FIG. 2 indicates briefly the methods used for the synthesis of TCPB and MDPPE.

Synthesis of Propynyl Ethers. 1,2,4-trichlorophenyl-3-(2-propynyloxy) benzene (TCPB) and 1-(2-propynyloxy) methylenedioxyphenyl ether (MDPPE) were synthesized by the method of F. Albericio et al., "Preparation and Application of the 5-(4-(9-Fluorenylmethyloxy carbonyl)-Aminomethyl-3,5-Dimethoxyphenoxy)-Valeric Acid Handle for the Solid Phase Synthesis of C-Terminal Peptide Amides under Mild Conditions," *J. Org. Chem.* vol. 55, pp. 3730–3743 (1990) (FIG. 2). A mixture of 2,3,6-trichlorophenol or methylenedioxyphenol (0.05 mole), potassium tert-butoxide (6.16 g, 0.055 mole), propargyl bromide (6.6 g, 0.055 mole) in dry DMF (60 mL) was heated and stirred at 110° C. for 5 h, after which the solvent was removed under high vacuum. Ethyl acetate was added, the inorganic salts were removed by filtration, and the organic extract was washed sequentially with water, 2 M NaOH, and saturated aqueous NaCl. The organic phase was dried overnight (Na$_2$SO$_4$) to give a crude product. MDPPE, a liquid product, was purified by silica gel chromatography using hexane-ethyl acetate (7:3) as the eluting solvent. Yield: 6.5 g (74%). $^1$H NMR (CDCl$_3$): d 2.54 (t, 1H, CH), 4.61 (d, 2H, —OCH$_2$—), 5.92 (s, 2H, —OCH$_2$O—), 6.38–6.73 (m, 3H, aromatics). GC-MS (m/z): M$^{+\cdot}$=176.

TCPB, a solid product, was recrystallized from ethyl ether-hexane. Yield: 7.6 g (65%). Melting point, 58–59° C. (reference m.p., 57–59° C.). $^1$H NMR (CDCl$_3$): d 2.54 (t, 1H, CH), 4.80 (d, 2H, —OCH$_2$—), 7.24 (br, 1H, aromatics). GC-MS (m/z): M$^{+\cdot}$236.

Biological Assays. Fifth stadium larvae (day 1) weighing 180±20 mg were treated on the mid-thoracic dorsum with 1 μl of compound (in acetone) or acetone alone (control). Dose-mortality relationships for each compound were measured using triplicate assays with ten larvae per replicate, and five doses of compound per determination (one dose per larva). Median lethal dose ($LD_{50}$) and 95% fiducial limits (FL) were computed by probit analysis using SAS software (SAS Institute Co., Cary, N.C., 1985). Resistance ratios (RR) were calculated as the ratio of $LD_{50}$ for Pyr-R larvae to $LD_{50}$ of LSU larvae. For synergist bioassays, nontoxic pyrethroid isomers, PBO, TCPB, MDPPE, or DEF was applied to the dorsal surface of the mid-abdomen thirty min prior to applying cypermethrin to the mid-thoracic dorsum. Control larvae were treated with the appropriate concentration of synergist, or with acetone alone. Synergism ratios (SR) were calculated as the ratio of $LD_{50}$ for the toxin alone to $LD_{50}$ for the toxin plus the synergist. After treatment, larvae were maintained at 27° C., and mortality was recorded after 72 h. The criterion for mortality was absence of coordinated movement within 30 s after being prodded with a pencil.

RESULTS

Biological activity of pyrethroids. Susceptibility to pyrethroids was measured in bioassays on both pyrethroid-susceptible (LSU) and pyrethroid-resistant (Pyr-R) larvae. See Table 3. For LSU larvae, fenfluthrin isomers and pyrethroid analogs were less toxic than cypermethrin, with $LD_{50}$s ranging from 1.06 μg/larva (for fenfluthrin 3) to 57.5 μg/larva (for compound 7), as compared with 0.05 μg/larva for cypermethrin. For 8 of the 15 compounds, no toxicity was measured following treatment with 100 μg/larva.

TABLE 3

Toxicity of pyrethroids in topical bioassays with pyrethroid-susceptible (LSU) and pyrethroid-resistant (Pyr-R) strains of H. virescens

| Com-pound[a] | LSU $LD_{50}$[b] | FL[c] | slope | Pyr-R $LD_{50}$ | FL | slope | RR[d] |
|---|---|---|---|---|---|---|---|
| Cypermethrin | 0.05 | 0.04–0.06 | 2.52 | 2.91 | 2.36–4.06 | 2.20 | 58.2 |
| Fenfluthrin 2 | 1.46 | 1.19–1.86 | 2.34 | 4.16 | 3.57–4.92 | 3.40 | 2.85 |
| Fenfluthrin 3 | 1.06 | 0.92–1.24 | 3.55 | 2.92 | 2.62–3.31 | 4.67 | 2.75 |
| 2 | 9.44 | 7.57–12.5 | 2.36 | >130[e] | — | — | >13.8 |
| 3 | 4.85 | 3.85–6.39 | 2.17 | 117 | 91.4–171 | 2.65 | 24.1 |
| 5 | >150[e] | — | — | NT | — | — | — |
| 7 | 57.5 | 39.3–112 | 1.44 | NT | — | — | — |
| 12 | 1.14 | 0.91–1.42 | 2.32 | 51.3 | 38.3–84.7 | 1.69 | 45.0 |

[a]Fenfluthrin 1 and Compounds 1, 4, 6, 8, 9, 10, and 11 were non-toxic (NT) at a dose of 100 μg/larva in bioassays on both LSU and Pyr-R insects.
[b]$LD_{50}$ values are expressed as μg/larva, and were computed by probit analysis.
[c]FL = 95% fiducial limits
[d]RR = $LD_{50}$ for Pyr-R strain/$LD_{50}$ for LSU strain.
[e]For Compounds 2 and 5, levels of mortality were 13.3 and 58% at the highest doses tested (130 and 150 μg/larva, respectively).

Stereochemistry about C-1 was a major determinant of toxicity: all 1R enantiomers tested were toxic, while no 1S enantiomers were toxic.

For α-cyano-containing compounds (4–12), αS, 1-enantiomers were toxic, while a)R, 1R and αR, 1S enantiomers were not. In addition, susceptibility was always greater for 1, cis than for 1R, trans isomers.

For non-cyano, methylenedioxyphenyl (MDP)-containing compounds, biological activity of 3 (the cis isomer) was almost twice as high as 2 (the trans isomer). Likewise, for toxic propargyloxyphenyl (PP) compounds, the cis isomer (12) was over 50 times more toxic than the trans isomer (7). By contrast, for toxic fenfluthrin isomers there were no significant differences in $LD_{50}$s between the trans and cis isomers (1.46 and 1.06 μg/larva for fenfluthrin 2 and 3, respectively).

Cypermethrin was the most toxic pyrethroid in tests with Pyr-R insects, but the resistance ratio for cypermethrin was substantially higher than that of most of the other toxic pyrethroids tested (Table 3). Whereas the $LD_{50}$ for cypermethrin for this strain (2.91 μg/larva) was 58 times higher than that measured for LSU larvae, RRs were low for fenfluthrin isomers (2.85 and 2.75 for 1R, trans and 1R, cis fenfluthrin, respectively), intermediate for the 1R, cis MDP compound (3; RR=24), and high for αS, 1R-PP (12; RR 45). As was true for the LSU larvae, Pyr-R insects were more susceptible to cis isomers than to trans isomers of the toxic compounds.

Synergism of pyrethroid toxicity. In bioassays with LSU larvae, no substantial synergism was observed for any of the non-toxic pyrethroid isomers, nor for any of the conventional synergists.

By contrast, all compounds tested increased the susceptibility of Pyr-R larvae to cypermethrin. See Table 4. The propynyl ether TCPB was the most effective synergist, with an SR of 4.69. Of the other PP-containing compounds tested, only 11 (αR, 1R, cis PP) substantially enhanced the toxicity of cypermethrin (SR=2.55). Co-application of cypermethrin and 6, the αR, 1R, cis MDP compound, increased cypermethrin toxicity by a factor of 2.69, which was greater than synergism with PBO (SR=1.97). Relative to PBO and TCPB, synergism with MDPPE, which contains both MDP and PP side chains, was intermediate (SR =2.65). Finally, substantial synergism (SR =4.04) was seen with the esterase inhibitor DEF.

The synergism of cypermethrin toxicity with nontoxic pyrethroids in Pyr-R larvae varied by isomer. See Table 4. Among the 4 PP-containing compounds evaluated, only 11 (αR, 1R, cis PP) had a substantial synergistic effect on cypermethrin toxicity (SR=2.55); the corresponding trans isomer (8) did not. Further, the structurally related compounds 9 (αR, 1S, trans PP) and 10 (αS, 1S, trans PP), were inactive as synergists. Of the MDP-containing compounds, synergism of cypermethrin toxicity was greater with 6 (αR, 1R, cis; SR=2.69) than with PBO (SR=1.97), and no synergism was measured with compound 1 (1S, trans, no OxCN) in Pyr-R larvae. Finally, in tests with isomers of fenfluthrin and conventional synergists in Pyr-R insects, toxicity of the 1R, cis isomer (fenfluthrin 3) was not increased by co-application of either PBO or DEF (SR =0.86 or 0.91, respectively), but did increase slightly with TCPB (SR=1.47). However, in tests with the 1R, trans isomer (fenfluthrin 2), slightly higher synergism was measured with TCPB and DEF (SR=1.83 and 1.33, respectively).

TABLE 4

Synergism of pyrethroid toxicity in pyrethroid-susceptible (LSU) and -resistant (Pyr-R) H. virescens[a]

| | LSU | | | | Pyr-R | | | |
|---|---|---|---|---|---|---|---|---|
| | $LD_{50}$[b] | FL | slope | SR[c] | $LD_{50}$ | FL | slope | SR |
| Cypermethrin plus: | | | | | | | | |
| PBO | 0.04 | 0.03–0.05 | 2.18 | 1.25 | 1.48* | 1.08–2.34 | 2.14 | 1.97 |
| TCPB | 0.04 | 0.03–0.07 | 1.60 | 1.25 | 0.62* | 0.48–0.78 | 2.46 | 4.69 |
| MDPPE | 0.06 | 0.04–0.09 | 1.70 | 0.83 | 1.10* | 0.83–1.67 | 2.31 | 2.65 |
| DEF | 0.05 | 0.03–0.08 | 1.31 | 1.00 | 0.72* | 0.57–0.92 | 2.62 | 4.04 |
| Fenfluthrin 1 | 0.05 | 0.04–0.07 | 1.59 | 1.00 | 2.07 | 1.48–5.61 | 2.49 | 1.41 |
| 1 | 0.05 | 0.04–0.06 | 2.71 | 1.00 | 1.74 | 1.37–2.82 | 3.32 | 1.67 |
| 6 | 0.05 | 0.04–0.06 | 2.37 | 1.00 | 1.08* | 0.79–1.71 | 2.12 | 2.69 |
| 8 | 0.06 | 0.05–0.08 | 2.39 | 0.83 | 1.84 | 1.35–4.11 | 2.49 | 1.58 |
| 9 | 0.04 | 0.03–0.05 | 2.76 | 1.25 | 1.80 | 1.22–8.54 | 1.81 | 1.62 |
| 10 | 0.04 | 0.03–0.06 | 2.81 | 1.25 | 2.55 | 1.66–5.61 | 2.22 | 1.14 |
| 11 | 0.04 | 0.03–0.04 | 3.28 | 1.25 | 1.14* | 0.86–1.74 | 2.33 | 2.55 |
| Fenfluthrin 2 plus: | | | | | | | | |
| TCPB | 1.21 | 1.01–1.44 | | 1.21 | 2.27 | 1.78–2.73 | 3.57 | 1.83 |
| DEF | 1.17 | 0.97–1.45 | | 1.24 | 3.12 | 2.51–4.11 | 3.31 | 1.33 |
| Fenfluthrin 3 plus: | | | | | | | | |
| PBO | 1.39 | 1.15–1.75 | 3.59 | 0.76 | 3.41 | 2.95–4.20 | 4.62 | 0.86 |
| TCPB | 1.23 | 1.02–1.49 | 3.93 | 0.86 | 1.98 | 1.62–2.64 | 4.37 | 1.47 |
| DEF | 0.94 | 0.78–1.12 | 4.27 | 1.13 | 3.21 | 2.74–3.93 | 4.40 | 0.91 |

[a]Compounds were applied to the third abdominal dorsum 30 min. prior to application of fenfluthrin or cypermethrin. Doses of compounds were 50 μg/larva except for compound 11 (25 μg/larva).
[b]μg cypermethrin or cis, 1R- fenfluthrin per larva. Asterisks signify values that are significantly different from those measured in tests with toxin only.
[c]SR = synergism ratio ($LD_{50}$ of insecticide/$LD_{50}$ of insecticide with synergist).

The insecticidal activity and synergism of cypermethrin toxicity in bioassays with fenfluthrin and structurally-modified pyrethroids confirmed that enhanced metabolism is associated with pyrethroid resistance in the resistant Pyr-R strain of H. virescens. An isomer of fenfluthrin, in which potential sites for oxidative metabolism were blocked, was as toxic as cypermethrin to pyrethroid-resistant H. virescens. In addition, resistance ratios were higher for cypermethrin than with compounds in which the metabolically labile phenoxyphenyl group was replaced with MDP or PP, although the overall activities of compounds with these groups were not as effective as that of fenfluthrin.

The conclusion that P450 monooxygenases are involved in resistance was further supported by the studies with synergists. Cypermethrin toxicity was increased by the co-application of compounds containing PP or MDP functional groups, and the synergism of toxicity was greatest with the propynyl ether TCPB.

Synergism was lower in the tests with PBO than those with TCPB, which supports the conclusion that different classes of P450 monooxygenase are involved in resistance-associated metabolism of pyrethroids. Toxicity of cypermethrin was increased significantly following co-application of DEF, which suggests additional involvement of esterases in pyrethroid resistance.

Subsequent studies examining the metabolic fate of radiolabelled cypermethrin have confirmed the role of esterases in resistance. These preliminary results (data not shown) suggest that the insecticidal activity of fenfluthrin, and the utility of fenfluthrin as a diagnostic reagent, may result from fenfluthrin's unsuitability as a substrate for resistance-associated esterases. Whether resistance is based on a resistant oxidase or on a resistant esterase, the technique described here may be used to diagnose the presence of a metabolically-based resistance mechanism.

Insecticidal and synergistic activity of pyrethroids was dependent on the chemical configuration about the C-1 and a carbons. No significant toxicity or synergism was observed with 1S isomers. The 1R, cis isomers were more toxic than the corresponding trans isomers. In addition, toxicity of 1R-fenfluthrin was slightly higher with the cis isomer (fenfluthrin 3) than with the trans isomer (fenfluthrin 2) in both pyrethroid-susceptible and -resistant insects. Finally, only 1R, cis (but not trans) chrysanthemates containing MDP (6) or PP (11) groups had a significant synergistic effect on cypermethrin toxicity. At the a carbon, only S enantiomers (5, 7, 12) were toxic, while the corresponding αR, cis enantiomers (6 and 11) were synergists. Assuming that synergism results from P450-monooxygenase inhibition, these results show that interaction between these enzymes and synergists is stereospecific. While cypermethrin toxicity was enhanced by DEF, no significant synergism was observed when DEF was co-applied with either of the toxic fenfluthrin isomers (fenfluthrin 2 and fenfluthrin 3). This observation suggests that fenfluthrin is a poor substrate for resistance-associated esterases and oxidases.

Fenfluthrin toxicity was not synergized significantly by PBO, TCPB, or DEF, confirming that the phenoxybenzyl group is a primary site of attack in metabolically resistant *H. virescens*.

The relatively low toxicities of the compounds reported here probably make them impractical for widespread direct use as pest control agents. However, fenfluthrin 2, fenfluthrin 3, and compound 3, which lack the metabolically sensitive sites of other pyrethroids, are useful diagnostic compounds to monitor metabolic-associated resistance in field populations of *H. virescens* and *H. zea*.

For example, the following procedure could be used to diagnose resistance mechanisms in a field population. For convenience, the assays may use male insects collected from pheromone traps known in the art. The first assay establishes whether the insects are resistant to cypermethrin (or other pyrethroid used in the field). Scintillation vials (15 mL each) are coated with 10 μg cypermethrin (or other pyrethroid) per vial. One insect is placed in each vial. If an insect is still alive after 24 hours in the vial, it is considered to be resistant to the pyrethroid.

The second assay provides information about the resistance mechanism. Survivors from the first assay are placed in similar vials coated with 0.35 μg fenfluthrin 2 or 3, or with 1.0 μg compound 3. If an insect is dead after 24 hours in the vial, one concludes that the mechanism responsible for resistance was metabolic. If an insect is still alive after 24 hours, then another resistance mechanism is in effect (either alone or in conjunction with metabolic resistance).

Once a resistance mechanism has been diagnosed, the resistant population can be better managed. For example, a population expressing metabolic resistance could be treated by adding a synergist such as PBO, TCPB, or DEF to the cypermethrin; while reduced target site sensitivity could be treated by switching to a different chemical class of insecticide, such as a carbamate.

This invention may be used to diagnose metabolic resistance to pyrethroids in any of the insects for which pyrethroid insecticides are used, including dipterans, homopterans, lepidopterans, blattarians, hymenopterans, hemipterans, isopterans, and coleopterans; including by way of example and not limitation house flies, stable flies, horn flies, cockroaches, ants, termites, stink bugs, cotton bollworms, mosquitoes, aphids, white flies, and the various beetles that are agricultural pests.

As used in the specification and claims, an "effective amount" of a particular pyrethroid compound (other than a pyrethroid against which a field insect population has acquired resistance, the "field pyrethroid") is an amount of that compound that causes a statistically significant (P<0.05) difference in mortality rates between: (1) a population of insects that exhibits a metabolic-based resistance to the field pyrethroid, and that exhibits no substantial resistance mechanism to the field pyrethroid other than a metabolic-based resistance; and (2) a population of the same insect species that exhibits a substantial resistance mechanism to the field pyrethroid other than (or in addition to) a metabolic-based resistance. The arithmetic mean of the mortality rates of populations (1) and (2) is termed the "discriminatory percentage" Preferably, the "effective amount" is an amount equal to at least $LD_{99}$ for the compound as applied to population (1), but that is less than $LD_{10}$ for population (2).

Resistance to the field pyrethroid in such a population, in turn, refers to the resistance exhibited by a population of the species for which the 95% fiducial limits of the $LD_{50}$ for the field pyrethroid do not overlap the 95% fiducial limits of the $LD_{50}$ of the field pyrethroid for a wild-type population of the species that has not been exposed to a significant amount of pyrethroid insecticides.

As used in the specification and claims, an "effective amount" of a field pyrethroid is an amount equal to or greater than the $LD_{50}$ of the field pyrethroid when used in the bioassay described above for a wild-type population of the insect species that has not been exposed to a significant amount of pyrethroid insecticides.

By way of example and not limitation, the F. progeny of the LSU×Pyr-R cross selected with 1.0 μg cypermethrin per third stadium larva as described in the specification above are considered to be a population of *Heliothis virescens* that exhibits a metabolic-based resistance to cypermethrin, and that exhibits no substantial resistance mechanism to cypermethrin other than a metabolic-based resistance.

(Note that the "effective amount" is defined relative to a reference population having certain characteristics, and not, in general, with respect to a particular resistant population found in the field. After initial determination of the "effective amount" for a compound, testing the compound against a field-resistant strain is not generally performed to determine the "effective amount." Rather, a predetermined "effective amount" of the compound is applied to insects from the field-resistant strain o diagnose whether the resistance mechanism of the field strain is solely metabolic, or is based at east in part upon a non-metabolic resistance mechanism.)

As used in the specification and claims, an "effective amount" of a particular synergist for a particular pyrethroid compound is an amount of the synergist that reduces to a statistically significant degree the "effective amount" of the pyrethroid compound (as previously defined) when the synergist and the pyrethroid compound are both administered to a population of insects.

Halogens other than chlorine may be substituted in the dichlorovinyl moiety of pyrethroid compounds, for example dibromo-, difluoro-, diiodo-, or bromochloro-vinyl. Thus, unless clearly indicated otherwise, the term "fenfluthrin" in the Claims should be construed to encompass homologues of fenfluthrin that contain another dihalovinyl moiety in lieu of the dichlorovinyl moiety of fenfluthrin.

To enhance photostability of the compounds used in this invention, the compounds may be stored in amber glass containers; or preservatives such as p-aminobenzoic acid may be added.

Abbreviations Used in the Specification: CMDP: α-cyano methylenedioxyphenyl methyl; CPP: α-cyano propargyloxyphenyl methyl; DCC: dicyclohexylcarbodiimide; DEF: S,S,S-tributyl phosphorotrithioate; DMAP: N,N-dimethylaminopyridine; DMF: N,N- dimethyl formamide; FL: 95% fiducial limits; IRM: insecticide resistance management; MDP: methylenedioxyphenyl; PA: 3-(2,2-dichlorovinyl)-2,2-dimethylcyclopropane carboxylic acid or permethric acid; PBO: piperonyl butoxide; MDPPE: methylenedioxyphenyl propynyl ether; PFP: pentafluorophenyl; PP: propargyloxyphenyl; TCPB: 2,3,6-trichlorophenyl propynyl ether; RR: resistance ratio; SR: synergism ratio.

The complete disclosures of all references cited in this specification are hereby incorporated by reference. In the event of an otherwise irreconcilable conflict, however, the present specification shall control.

We claim:

1. In a population of dipteran, homopteran, lepidopteran, blattarian, hymenopteran, hemipteran, isopteran, or coleopteran insects exhibiting resistance to a pyrethroid insecticide;

a method of diagnosing whether the pyrethroid resistance results from a metabolically-based resistance mechanism;

said method comprising exposing pyrethroid-resistant insects from the population to an effective amount of a compound selected from the group consisting of trans, 1R-fenfluthrin; cis, 1R-fenfluthrin; and cis, 1R-methylenedioxyphenyl-3-(2,2-dihalovinyl)-2,2-dimethylcyclopropanecarboxylate; and observing the fraction of exposed insects that are killed by said exposing step;

whereby the results of said diagnostic method indicate that a metabolic mechanism is primarily responsible for the resistance if at least a discriminatory percentage of the insects is killed by said exposing step; and that a mechanism other than a metabolic mechanism, either alone or in conjunction with a metabolic mechanism, is responsible for the resistance if less than a discriminatory percentage of the insects is killed by said exposing step.

2. A method as recited in claim 1, wherein the compound is trans, 1R-fenfluthrin.

3. A method as recited in claim 1, wherein the compound is cis, 1R-fenfluthrin.

4. A method as recited in claim 1, wherein the compound is cis, 1R-methylenedioxyphenyl-3-(2,2-dihalovinyl)-2,2-dimethylcyclopropanecarboxylate.

5. A method as recited in claim 1, wherein the insects are a population of *Heliothis virescens*.

6. A method as recited in claim 1, wherein the insects are a population of *Helicoverpa zea*.

7. A method as recited in claim 1, wherein the insects are a population of *Helicoverpa annigera*.

8. A method as recited in claim 1, wherein said exposing step comprises placing insects into a container coated with an effective amount of the compound.

9. A method as recited in claim 1, additionally comprising the step of assaying the insects for resistance to the pyrethroid insecticide.

10. A method as recited in claim 1, wherein the insects exhibit resistance to cypermethrin.

11. A method as recited in claim 1, wherein the effective amount is at least $LD_{99}$ for the compound as applied to a reference population of insects that exhibits a metabolic-based resistance to the pyrethroid insecticide, and that exhibits no substantial resistance mechanism to the pyrethroid insecticide other than a metabolic-based resistance.

* * * * *